Figure 1:
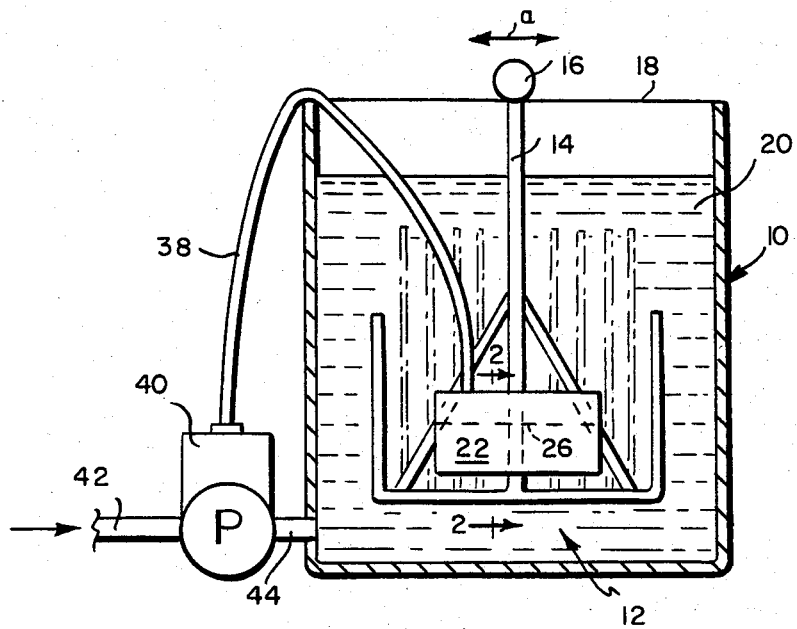

United States Patent [19]

Castner

[11] Patent Number: 4,499,852
[45] Date of Patent: Feb. 19, 1985

[54] APPARATUS FOR REGULATING PLATING SOLUTION IN A PLATING BATH

[75] Inventor: B. Christian Castner, Westford, Mass.

[73] Assignee: Shipley Company Inc., Newton, Mass.

[21] Appl. No.: 169,129

[22] Filed: Jul. 15, 1980

[51] Int. Cl.³ .............................................. B05C 11/10
[52] U.S. Cl. .................................. 118/690; 118/691; 118/425; 250/573
[58] Field of Search ............... 118/689, 690, 691, 425; 250/573, 577; 356/414; 137/93; 427/8, 345

[56] References Cited

U.S. PATENT DOCUMENTS

| | | | |
|---|---|---|---|
| 3,369,524 | 2/1968 | Fuhrer | 118/691 |
| 3,412,667 | 11/1968 | Hunt | 118/425 X |
| 3,475,316 | 10/1969 | Vittorio | 118/690 X |
| 3,532,519 | 10/1970 | Hirohata et al. | 427/8 |
| 3,734,629 | 5/1973 | Griffiths et al. | 250/573 X |
| 3,851,976 | 12/1974 | Meier | 356/414 X |
| 3,934,054 | 1/1976 | Schmeling et al. | 427/345 X |
| 4,156,149 | 5/1979 | Vaccari | 250/577 |

Primary Examiner—John P. McIntosh
Attorney, Agent, or Firm—Robert L. Goldberg

[57] ABSTRACT

Apparatus for maintaining the concentration of components of a plating solution substantially constant during use of a plating bath. The apparatus comprises a sensor suspended in the plating bath responsive to the concentration of one or more plating components of the plating solution. The sensor is capable of generating a signal whereby replenished solution is pumped to the solution to replace depleted components.

10 Claims, 2 Drawing Figures

APPARATUS FOR REGULATING PLATING SOLUTION IN A PLATING BATH

BACKGROUND OF THE INVENTION

When plating articles with metal, e.g., copper, maintaining the concentration of the solution components relatively constant during use of the plating solution is important in order to provide uniform results from metal deposit to deposit. Since various plating components are continuously depleted from the solution, either by plate-out or by chemical reaction, it is necessary to replenish the solution by addition of a replenisher composition containing one or more of the depleted components. The replenisher is typically in the form of a concentrated solution of the depleted components. Addition of such replenisher solutions is well known in the art.

To accomplish replenishment in accordance with the prior art, the plating solution is circulated by means of suitable plumbing from a plating tank through a "controller" apparatus designed to (1) detect the concentration of various of the components in solution and (2) signal any depletion in concentration to a pump capable of supplying replenisher solution to the plating tank. Such apparatus as is currently available is expensive, occupies a considerable amount of space and requires that the solution be removed from the bath before it is analyzed for concentration so that there is some delay in obtaining data which occassionally results in the bath becoming over-replenished.

It is the purpose of this invention to provide apparatus which will enable control of the concentration of components within the plating solution without the inherent disadvantages of the currently available controller apparatus.

SUMMARY OF THE INVENTION

As herein illustrated, the apparatus comprises one or more sensors responsive to the concentration of a given plating component in a metal plating solution, said sensor being suspended within the plating tank and being capable of generating a signal in response to the concentration of one or more solution components, means for supplying replenisher solution comprising one or more of the depleted components to the plating tank, said means being connected to a supply of said replenisher solution, and a pump connected to the means for supplying the replenisher solution to the tank operable in response to a signal from the sensor whereby the quantity of replenisher solution supplied is controlled. A rack within the plating tank supports the articles to be plated in the tank and such racks are generally provided with means for effecting oscillation of the rack. Desirably, the sensor is mounted on the rack for oscillation therewith. The sensor may be light or color sensitive and, when light sensitive, may comprise, for example, a silicone cell and light source supported and spaced apart sufficiently to allow the plating solution to circulate therebetween. Desirably, the component parts of the sensor are embedded in a transparent material such as Plexiglas and comprises a block containing an opening defining a passage open at its ends and at one side and bounded by spaced, parallel opposite sides of the passage in alignment with each other.

Figure 2:
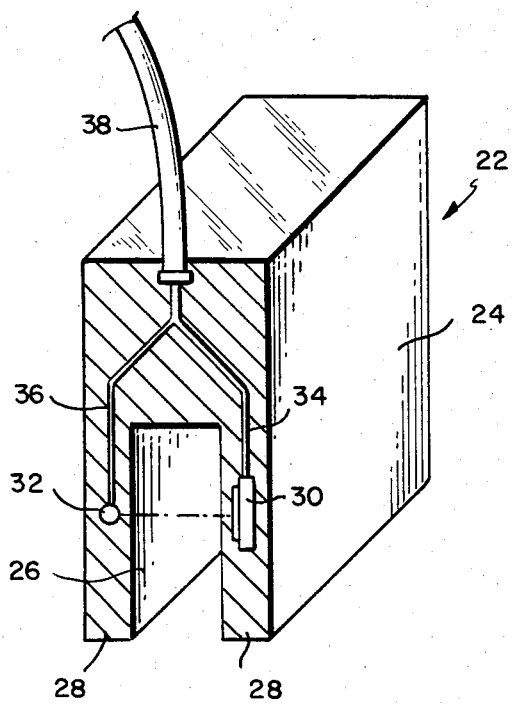

The invention will now be described in greater detail with reference to the accompanying drawings, wherein:

FIG. 1 diagramatically illustrates a plating tank showing a support rack therein for reciprocal movement and the apparatus of this invention for controlling the concentration of the plating solution; and FIG. 2 is a perspective view of the sensing unit for detecting the concentration of the plating solution taken on the section 2—2 of FIG. 1.

Referring to the drawings, FIG. 1, there is shown a plating tank 10 of substantially rectangular, horizontal and vertical section within which there is supported a plate supporting rack 12 suspended by hanger rods 14—14 on a rod 16 which rests on the upper edges 18—18 of the end walls of the tank for reciprocal movement as indicated by the double arrow a.

A plating solution designated 20 is maintained in the tank at a level such as to submerge the plates supported by the rack 12.

As heretofore pointed out, it is desirable to maintain a constant concentration of the components of the plating solution in the path so that uniform plating can be achieved and this heretofore has been achieved by continuously drawing off from the plating tank the plating solution and circulating it through apparatus for determining the concentration by light sensitive or color sensitive means which produce signals responsive to the depletion of the concentration in the solution, which signals, in turn, control operation of a pump for adding a replenisher solution to the bath to restore the bath components to their desired predetermined concentration. Such apparatus is expensive, takes up a considerable amount of room, requires that the plating solution be cooled, and adds significant delay in measurement. The purpose of this invention is to provide apparatus of much simpler construction for controlling the concentration of the solution, and as herein illustrated, the apparatus comprises, as shown in FIG. 2, a sensing device 22 in the form of a rigid, transparent block 24 of Plexiglas containing at its lower end an open-end groove of rectangular section which defines as elongate passage 26, at opposite sides of which there are spaced, parallel walls 28—28. As illustrated in FIG. 1, the passage 26 is positioned transversely on the tank, that is parallel to the direction of reciprocal movement, so that the reciprocal movement of the device with the rack will produce a flow of the solution in the passage first in one direction and then in the other to thus obtain a good sampling of the concentration of the solution within the tank. A sensor 30 is embedded in one of the walls 28 and in the other wall in alignment therewith is embedded a light bulb 32. Electrical conductors 34 and 36 connected, respectively, to the sensor and light bulb are also embedded in the block and extend therefrom to a flexible conduit 38 upwardly from the unit and out of the top of the tank.

The sensor 30, as herein show, is a silicone solar cell manufactured by Workmen Electronic Products, Inc., Sarasota, Fla. having an output voltage rating of 0.6 to 0.85 volts DC and an output current rating of 10 to 16 milliamps; however, an output rating of as low as 0.1 volts DC and 3 to 4 milliamps will suffice. The light bulb is rated at 12 volts and 2 watts. The width of the passage, that is, the gap between the walls 28—28, should be approximately ½ inch.

The flexible conduit 38 is connected to the control 40 of a pump P, the intake side of which is connected by a suitable conductor 42 to a source of replenisher solution, and the discharge side of which is connected by a suitable conductor 44 to the plating tank.

By way of example, the apparatus may be used to control the concentration of components within a plating solution for plating substrates such as circuit board base material with copper wherein the plating solution is an electroless copper plating solution comprising copper sulfate, complexing agent to maintain copper dissolved in solution, sodium hydroxide as a source of alkalinity and formaldehyde as a reducing agent. It is to be understood, however, that this particular solution is exemplary only and in no way limiting since the apparatus may be used for controlling the concentration of other plating solutions and components.

As herein illustrated, the sensor 22 determines the concentration of copper in the solution by colorimetry, that is, the degree to which the light from the light source penetrates through it to the solar cell. As copper is depleted from solution, at a given concentration, the sensor activates a pump which passes replenisher solution (in this case, concentrated complexed cupric ion) into the plating tank to replenish the solution to the extent necessary.

In operation, the rack 12 is oscillated at a rate of 10 to 12 cycles per minute, thus keeping the plating solution relatively uniform in concentration throughout the tank. Oscillation of the rack correspondingly oscillates the sensor so that the latter is, in turn, exposed to a fairly representative concentration of the solution in the tank. The signal from the sensor is transmitted through the conduit 38 to the control 40 which, in proportion to the signal received, controls the operation of the pump P so that the pump delivers a greater or lesser amount of concentrated solution to the tank depending upon the loss of concentration in the tank due to the plating operation. With this apparatus, a control of plus or minus 5% may be easily achieved.

While the block 24 is stated as being comprised of Plexiglas, it may be comprised of other rigid, inert, transparent or translucent material. Further, a light sensitive device other than a silicone solar cell may be employed and a light source other than an electric light bulb may be used.

It should be understood that the present disclosure is for the purpose of illustration only and includes all modifications or improvements which fall within the scope of the appended claims.

What is claimed is:

1. Apparatus for regulating the concentration of dissolved metal in an electroless plating bath comprising a sensor suspended in the bath responsive to the concentration of said dissolved metal and capable of generating a signal, means for oscillating the sensor in the bath, a pump for supplying replenisher solution to the bath, said pump being connected a supply of replenisher solution for said dissolved metal and to the sensor operable in response to the signal from the sensor to supply replenisher solution from said source to the path in sufficient quantity to compensate for the depletion of the dissolved metal removed during the plating operation.

2. The apparatus of claim 1 wherein the sensor comprises a structure of translucent material defining a passage bounded along its side by spaced, parallel walls and open at the bottom, a light responsive cell embedded in one of the walls, a light source embedded in the other of the walls in alignment with the cell and current conducting elements embedded in the structure at their places of connection to the cell and light source.

3. Apparatus according to claim 2 wherein the sensor is light sensitive.

4. Apparatus according to claim 2 wherein the sensor is color sensitive.

5. Apparatus according to claim 2 wherein an oscillatable rack supports the articles to be plated in the path and the sensor is mounted on a rack for oscillation therewith.

6. Apparatus according to claim 2 wherein the sensor comprises a silicone solar cell and a light bulb supported spaced apart therefrom sufficient to allow the plating solution to circulate between them.

7. Apparatus according to claim 6 wherein the silicone solar cell and light bulb are supported at a spacing of approximately ½ inch.

8. Apparatus according to claim 6 wherein the silicone cell has an output voltage of at least 0.1 Vdc and an output current of 3 to 4 mA and the light bulb has a rating of 12 V and 2 W.

9. Apparatus according to claim 6 wherein the silicone solar cell and light bulb are embedded in Plexiglas.

10. The apparatus of claim 1 where the sensor is responsive to dissolved copper.

* * * * *